United States Patent [19]

George et al.

[11] 3,979,948

[45] Sept. 14, 1976

[54] APPARATUS FOR DETERMINING THE DYNAMIC COMPLEX HARDNESS OF RESILIENT ROLL COVERINGS

[75] Inventors: Harvey F. George, W. Hempstead; Charles G. Marrara, Franklin Square; Robert H. Oppenheimer; David W. Cairns, both of Glen Cove, all of N.Y.

[73] Assignee: Gravure Research Institute, Inc., Port Washington, N.Y.

[22] Filed: Sept. 8, 1975

[21] Appl. No.: 611,265

[52] U.S. Cl. .................................... 73/78; 73/81; 73/89
[51] Int. Cl.² ........................................ G01N 3/32
[58] Field of Search ............... 73/78, 81, 91, 67.2, 73/67, 15.6, 89

[56] References Cited
UNITED STATES PATENTS

| | | |
|---|---|---|
| 3,256,741 | 6/1966 | Wise ........................................ 73/89 |
| 3,550,427 | 12/1970 | Sueyoshi ............................... 73/15.6 |

*Primary Examiner*—James J. Gill
*Assistant Examiner*—Anthony V. Ciarlante
*Attorney, Agent, or Firm*—Bryan & Bollo

[57] ABSTRACT

Apparatus for determining the dynamic complex hardness of resilient roll coverings including a portable housing for positioning directly on the resilient roll covering to be tested. The portable housing includes an adjustable probe coupled to force and displacement transducers. The adjustable probe is placed in contact with the resilient roll covering and vibrated. The transducers produce output signals in accordance with the force encountered by and displacement of the probe during displacement of the surface of the resilient roll covering. The output signals from the transducers are coupled to dynamic hardness and loss angle circuitry for providing direct measurements of the magnitude and phase angle of the dynamic complex hardness.

12 Claims, 8 Drawing Figures

APPARATUS FOR DETERMINING THE DYNAMIC COMPLEX HARDNESS OF RESILIENT ROLL COVERINGS

The present invention relates to apparatus for determining viscoelastic properties of resilient coverings, and more specifically to an apparatus for determining the dynamic complex hardness of resilient roll coverings, such as rubber coverings for gravure printing rolls.

Various apparatus are known for measuring viscoelastic properties. See, for example, U.S. Pat. Nos. 3,126,579 (Janszen), 3,526,741 (Wise); 3,319,460 (Barigant); 3,417,608 (Barigant); 3,479,858 (Umeno et al.); 3,604,249 (Wilson); 3,638,230 (Umeno et al.); and 3,699,808 (Ford et al.). Such known apparatus are generally concerned with measuring the dynamic modulus and/or loss angle of pre-cut flat test samples having controlled dimensions, load applications, and excitation conditions, e.g., resonance, see the articles entitled, "A New Indentor Hysteresimeter" and "The Indentor Hysteresimeter For Testing Dynamic Properties," by G. Tangorra, appearing in *Rubber Chemistry & Technology*, 1961. Such known apparatus are not capable of directly measuring the dynamic complex hardness of resilient roll coverings, but rather measure the dynamic complex modulus or other parameters of flat test samples under controlled conditions. Moreover, these known apparatus are generally complex and costly, and designed for permanent placement, rather than portable testing.

Dynamic complex hardness is related to the complex modulus, but provides a truer indication of performance of a resilient roll covering in actual use. Further, measurement of this parameter provides a dynamic indication of the resistance to indentation of the resilient covering and is defined as

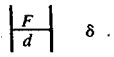

It is possible to derive a modulus from this dynamic hardness, but covering thickness, surface curvature, non-homogeneous rubber properties, etc., would have to be specified.

It is an object of the present invention to provide an apparatus for measuring the dynamic complex hardness of resilient roll coverings.

It is a further object of the present invention to provide an apparatus for measuring the dynamic complex hardness of ready to use gravure impression rolls.

It is a still further object of the present invention to provide a portable apparatus for measuring the dynamic complex hardness of gravure impression rolls.

It is a still further object of the present invention to provide an apparatus for directly measuring the dynamic complex hardness of gravure impression rolls.

It is a still further object of the present invention to provide a portable apparatus for measuring the dynamic complex hardness of gravure impression rolls which is of relatively compact design and low cost.

Other objects, aspects, and advantages of the present invention will be apparent when the detailed description is considered with the drawings.

Briefly, the apparatus in accordance with the present invention for measuring the dynamic complex hardness (magnitude and phase angle) of resilient roll coverings includes a housing for positioning directly on the resilient roll covering to be tested, an adjustable probe for contacting the resilient roll covering, force and displacement transducers coupled to the probe, an excitation circuit for energizing the transducers and receiving and conditioning the outputs therefrom, dynamic hardness and phase angle circuit means electrically coupled to the force and displacement transducers to receive output signals therefrom and provide a direct reading of the magnitude of the dynamic complex hardness and its phase or loss angle.

The present invention is illustrated in the accompanying drawings, in which:

FIG. 3 is a representative oscilloscope trace of the force and displacement outputs of the transducers showing the phase difference (loss angle) there between;

Figure 1:
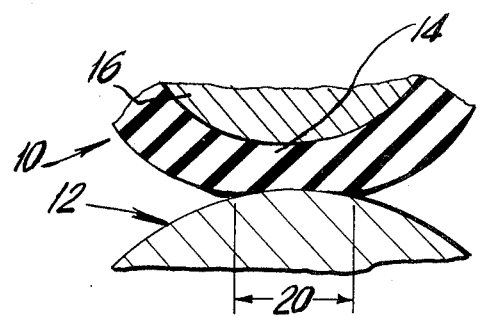
FIG. 1 is a partial sectional view of a gravure impression roll in engagement with a printing cylinder during the normal printing operation in a rotogravure printing press.

Referring to FIG. 1, a gravure impression roll 10 is shown in contact with a gravure cylinder 12. The impression roll 10 generally includes a rubber covering 14 bonded to a cylindrical steel core 16. It should be understood that the impression roll may include more than one rubber layer, as desired, and may be made of other resilient materials similar to rubber which exhibit volumetric incompressibility.

During a printing cycle in a rotogravure printing press, a web (not shown) is firmly pressed against the gravure cylinder 12 by the impression roll 10. Most of the energy used to drive the press is dissipated in the impression roll coverings which are subject to severe stresses and strains which affect the printing performance of the press and impression roll life. The nip 20 of the impression roll 10, i.e., the area of contact with the gravure cylinder 12 over which the maximum force is applied to the web or medium to be printed, is subject to the most severe stresses and strains. The increased used of wide presses operating at high speeds results in even more severe stresses and strains in the impression roll coverings and a corresponding higher rate of heat generation therein. As a result the usable life cycle of the impression roll coverings is further shortened and there is a higher incidence of poor press performance.

At present the main criteria for selection of materials for impression roll coverings and acceptance of impression roll coverings by printers are resistance to ink solvents, static hardness as measured by a Shore gauge, and in the case of rolls for electrostatic assist, electrical conductivity. However, these criteria are generally insufficient to predict actual press performance of impression roll coverings.

The Shore hardness is a static hardness and does not necessarily indicate what the real hardness of the impression roll covering will be under the dynamic conditions encountered at the gravure impression zone (nip). Nor do any of these acceptance criteria indicate what the heat build-up of a particular roll covering will be, its life, its web feed characteristics, or its effect on print quality. As all of these impression roll characteristics are related to the viscoelastic behavior of the covering materials, the importance of determining the viscoelastic properties of the impression rolls is apparent. Moreover, a determination of the dynamic complex hardness resulting from the application of compressive and shear strains to the impression roll 10 more closely resembles the actual roll loading in the press than individual shear or compression movements.

Figure 2:
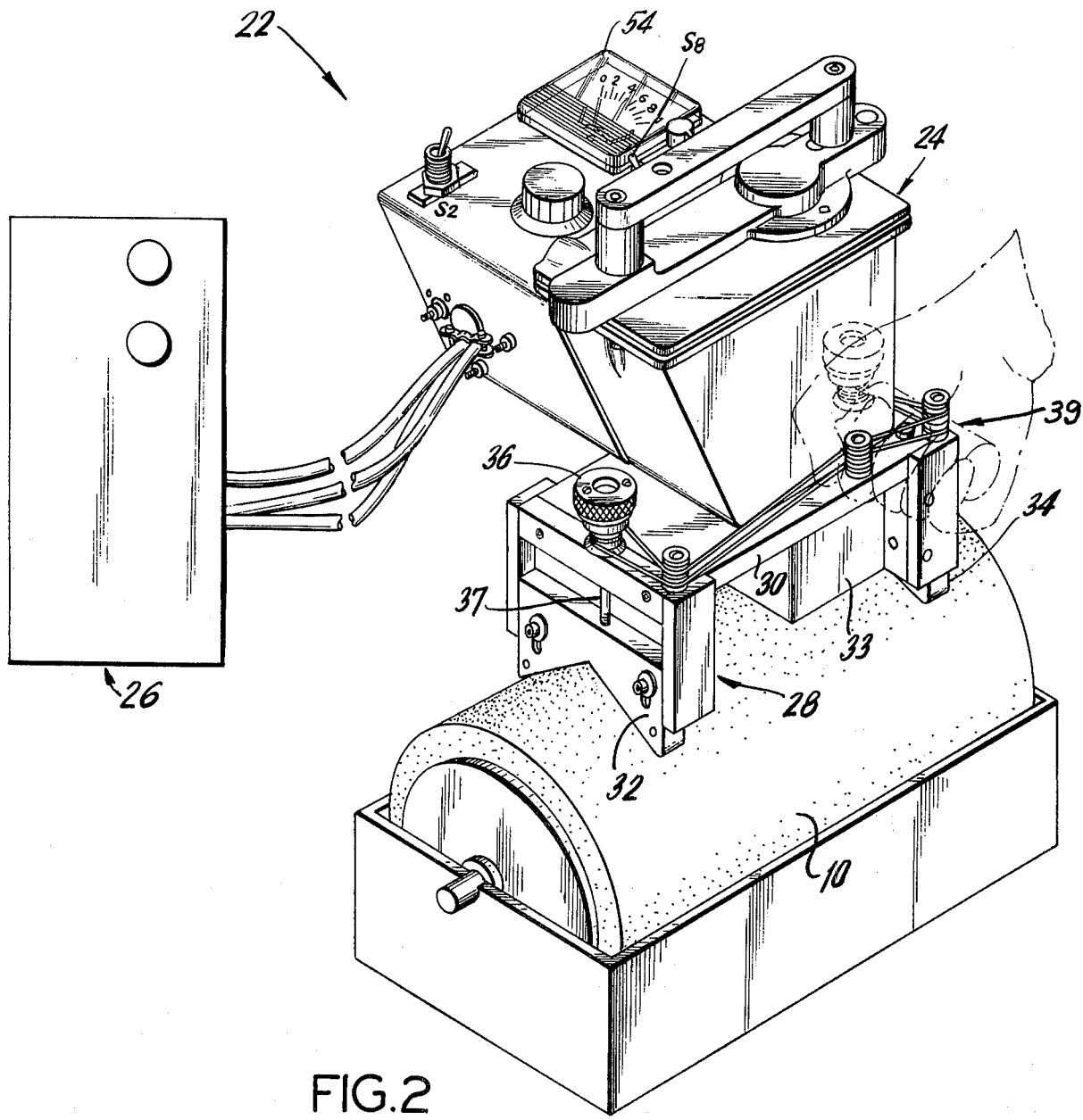
FIG. 2 is a perspective view of the apparatus according to the present invention with the vibrator section mounted directly on an impression roll covering for testing.

Referring to FIG. 2, the apparatus of the present invention is generally illustrated at 22. The apparatus 22 may be conveniently considered, for the purposes of description, to include a vibrator section 24 and a signal applying and processing section 26 electrically coupled to the vibrator section 24.

The vibrator section 24 is mechanically coupled to a V-block guide 28 which is dimensioned for mounting on the impression roll 10. The V-block guide 28 includes a central rectangular support 30 and two V-notched legs 32 and 34 coupled to the opposite ends of the central support 30 and extending downwardly therefrom. The V-notched legs 32 and 34 accept the impression roll 10 when the V-block guide 28 is positioned thereon. Moreover, the V-notched legs 32 and 34 may advantageously be mounted on a support plate (not shown) which includes a recess to accept flat rubber samples for testing by the apparatus 22.

A probe adjustment means 36, including a pair of threaded screws 37, couples the V-notched legs 32 and 34 to the central support 30. A pulley system 39 mechanically couples the threaded screws 37 to ensure that rotation of either of the threaded screws 37 produces the same movement in both legs 32 and 34 toward or away from the support 30.

A probe housing 33 is affixed to the central support 30 and extends downwardly through an orifice (not shown) in the central support 30. A probe 35 is arranged within the probe housing 33 and extends downwardly therefrom, see FIG. 3. Rotation of one of the threaded screws 37 places the probe 35 in contact with the impression roll 10 (zero reference) and then provides initial penetration of the probe 35 into the roll 10, e.g., a penetration of 6.5 mils, to ensure that the probe 35 is in engagement with the surface of the impression roll 10.

Figure 3:
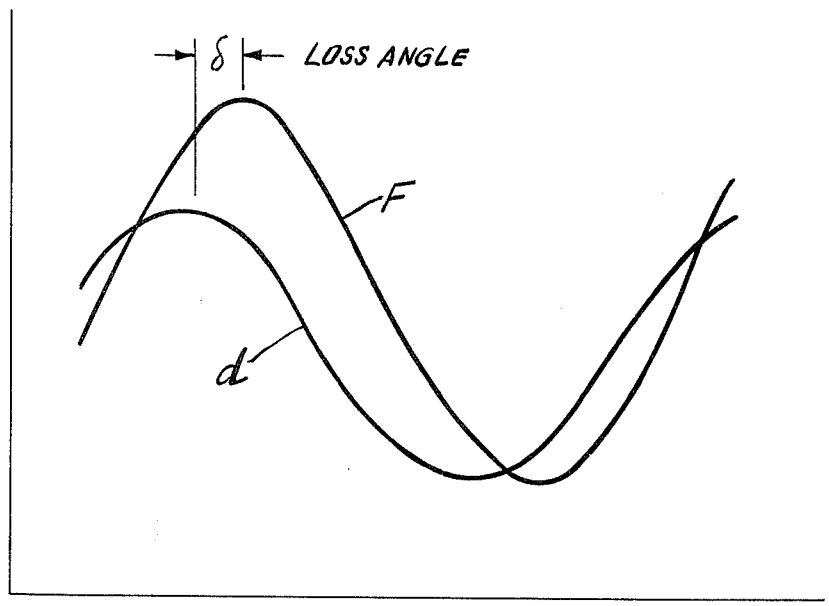

Referring to FIG. 3, the displacement of the probe 35 from its original position in response to signals from the vibrator section 24 (displacement of the surface of the rubber covering 14), and the force encountered by the probe 35 during penetration are shown graphically. The waveforms for $d$ and F are complex in nature having a loss angle $\delta$ therebetween.

Figure 4:
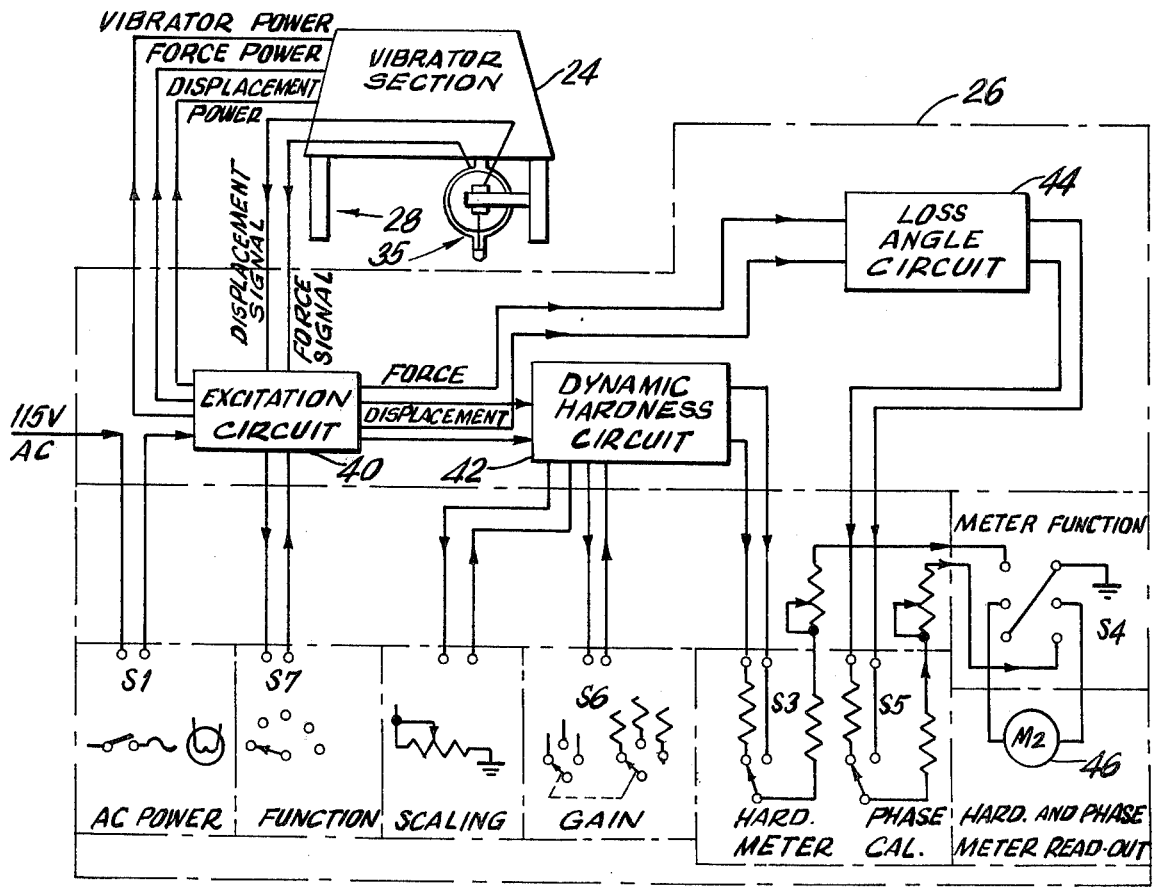
FIG. 4 is a schematic block diagram of the apparatus according to the present invention including the vibrator section, its excitation circuit, and the dynamic complex hardness measurement circuits.

Referring to FIG. 4, the general circuit arrangement for the apparatus 22 is illustrated. The vibrator section 24, which includes the probe 35, receives power from an excitation circuit 40 of the signal applying and processing section 26. The displacement and force signals from the vibrating probe 35 are transmitted to the excitation circuit 40 and then to a dynamic hardness circuit 42 and a phase or loss angle circuit 44. The output signals from the dynamic hardness circuit 42 and the loss angle circuit 44 are directly read on a two scale meter 46.

Figure 5:
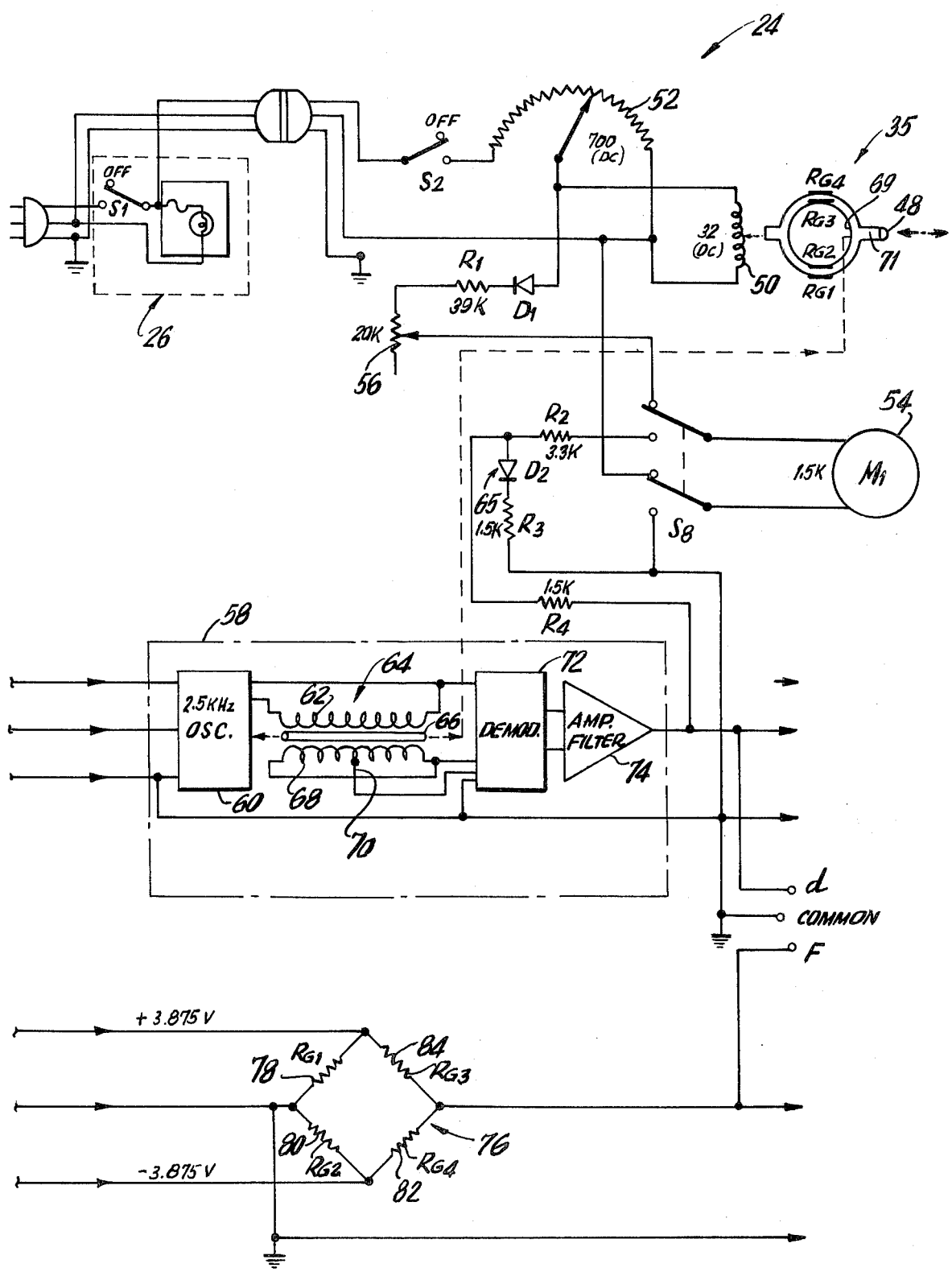
FIG. 5 is a detailed schematic diagram of the vibrator section circuitry.

Referring to FIG. 5, the vibrator section 24 is illustrated schematically. The probe 35 is preferably in the shape of a ring and advantageously includes a rounded or spherical contact portion 48. Other shapes for the contact portion 48, e.g., cylindrical and flat, may also be used, as desired. The ring probe 35 and its rounded contact portion 48 are driven by a vibrator coil 50 which is energized by the excitation circuit 40 when switches $S_1$ and $S_2$ are closed. Adjustment of a rheostat 52 controls the amount of alternating current, generally between about 10 and about 500 ma., supplied to the vibrator coil 50. A d.c. meter 54, see also FIG. 2, monitors the amount of current supplied to the vibrator coil 50. A potentiometer 56 provides calibration of the meter 54.

Excitation of the vibrator coil 50 causes the ring probe 35 to vibrate. The movement of the ring probe 35 is sensed by a displacement transducer 58 in the form of a linear variable displacement transformer (LVDT), commercially available from Schaevitz Engineering Co. as Model 050-DC-B. The transducer (LVDT) 58, which is affixed to the vibrator section 24, includes an oscillator 60, a transformer 64, a demodulator 72, and an amplifier-filter 74. The oscillator 60 oscillates at a frequency of 2.5 KHz for energizing the primary winding 62 of the transformer 64. A movable core 66 is positioned between the primary winding 62 and the secondary winding 68 and mechanically threaded to the inner surface 69 of the probe ring 35 at a point adjacent to and axially aligned with the contact portion 48 which is threaded into an outer projection 71 on the probe ring 35. The secondary winding 68 includes a center tap 70.

The output of the secondary winding 68 is applied to the demodulator 72 and then to the amplifier-filter 74. The output at the secondary winding 68 is a difference output voltage ($Vsec_1-Vsec_2$) which is directly proportional to the displacement of the transformer core 66 and therefore the linear displacement ($d$) of the probe 35 to which it is mechanically coupled. The linear displacement or amount of indentation ($d$) is directly related to the amount of strain applied to the impression roll 10. The output of the secondary winding 68 is also fed to a penetration circuit 65. When a switch $S_8$ is closed, the output of the penetration circuit 65 is fed to the meter 54 to provide a direct reading of the amount of indentation of the probe 35 into the roll covering 14.

A force transducer represented schematically at 76 includes four strain gauges 78, 80, 82 and 84 coupled to the ring probe 35. The strain gauges 78, 80, 82 and 84 are advantageously semiconductor strain gauges such as those available from Kulite Corporation which have a K of 130 and a resistance of approximately 337 ohms. The strain gauges 78, 80, 82, and 84 are electrically connected in a Wheatstone bridge configuration to produce electrical signals directly related to the force (stress) developed in the impression roll 10 during vibration of the ring probe 35. The strain gauges $Rg_1$–$Rg_4$ (78–84) are mounted on the ring probe 35 with gauges $Rg_2$ and $Rg_3$ mounted on the inner surface of the ring probe 35, diametrically opposite to one another, and gauges $Rg_1$ and $Rg_4$ mounted on the outer surface of the ring probe 35, diametrically opposite to one another and aligned with gauges $Rg_2$ and $Rg_3$. The gauges $Rg_1$–$Rg_4$ are affixed to the ring probe 35, e.g., with a conventional adhesive.

A variation in the load on the ring probe 35 caused by the resistance of the roll covering 14 during indentation will produce a resistance change in each strain gauge $Rg_1$–$Rg_4$, resulting in a change in the output voltage of the Wheatstone bridge. Since $Rg_1=Rg_4$ and $Rg_2=Rg_3$, and $Rg_1$ and $Rg_4$ are in identical tension under load and $Rg_2$ and $Rg_3$ are in identical compression under load, the voltage output of the Wheatstone bridge is directly proportional to the percentage resistance change in the strain gauges 78–84.

Figure 6:
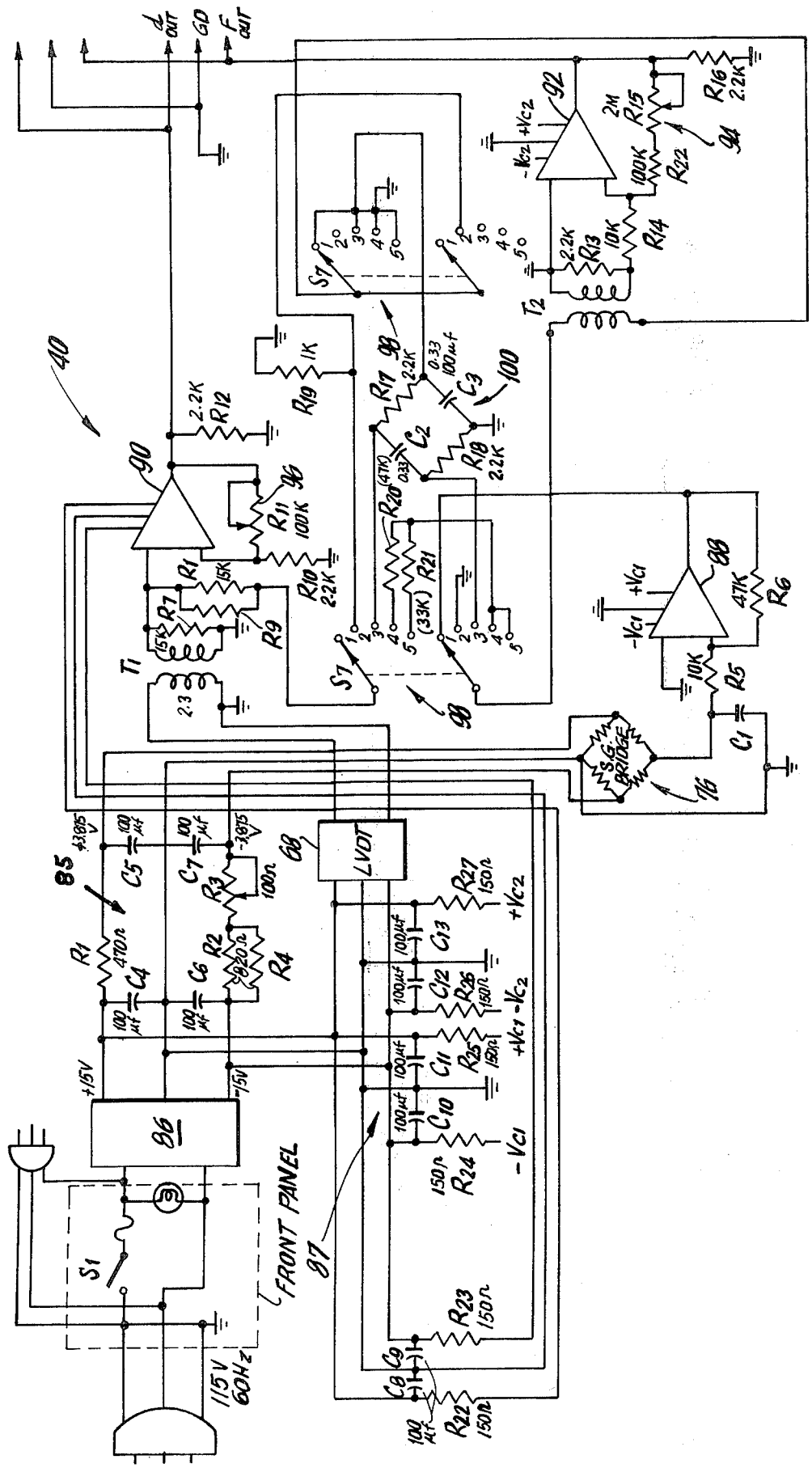
FIG. 6 is a detailed schematic diagram of the excitation circuit.

Referring to FIG. 6, the excitation circuit 40 is schematically illustrated. The excitation circuit 40 includes a power supply 86, such as the type commercially available from Teledyne/Philbrick as Model 2203. The power supply 86 produces an output voltage of ± 15 VDC which is transmitted to the displacement transducer 58 and also passed through suitable decoupling elements 87 to apply a bias voltage of ± 15 VDC to operational amplifiers 88, 90, and 92. Further, the output voltage from the power supply 86 is also passed through suitable attenuating and filtering elements 85 to provide a voltage of ± 3.875 VDC to the strain gauges 78–84.

With a ganged switch ($S_7$) 98 in the first position as shown in FIG. 6, electrically connected operational amplifiers 88 and 92, and feedback potentiometer 94, provide an adjustable gain of 50 to 500 for the input force signal (F) received by the amplifier 88. Operational amplifier 90 and its feedback potentiometer 96 provide an adjustable gain of 1 to 50 for the input displacement signal ($d$). The force and displacement signals are fed to the dynamic hardness circuit 42 and loss angle circuit 44 to provide a direct measurement of the magnitude and phase of the dynamic complex hardness on meter 46.

Switch positions 2–5 of ganged switch ($S_7$) 98 are used used to provide built-in test calibrations. When the ganged switch ($S_7$) 98 is moved to its second position, the input force signal is not received by the amplifier 88, but instead the input displacement signal is switched to the input of amplifier 92, which provides an attenuated displacement signal at the output of the amplifier 92. Amplifier 90 provides a normal displacement signal at its output. Thus, any phase difference in the outputs of amplifiers 90 and 92 is determined to establish a phase reference level.

When the ganged switch ($S_7$) 98 is moved into its third position the input displacement signal is switched through an R-C bridge phase shifter 100 prior to being transmitted to the amplifier 92. Thus, a phase shifted displacement signal is provided at the output of amplifier 92. Amplifier 90 provides a normal displacement signal at its ouput. Thus, a known phase angle δ is detected to determine if the apparatus 22 is operating accurately.

In the fourth and fifth positions of the switch 98, normal and attenuated displacement signals are provided at the output of the amplifiers 90 and 92, respectively, and fed to the dynamic hardness circuit 42 to provide predictable dynamic complex hardness ratios.

Figure 7:
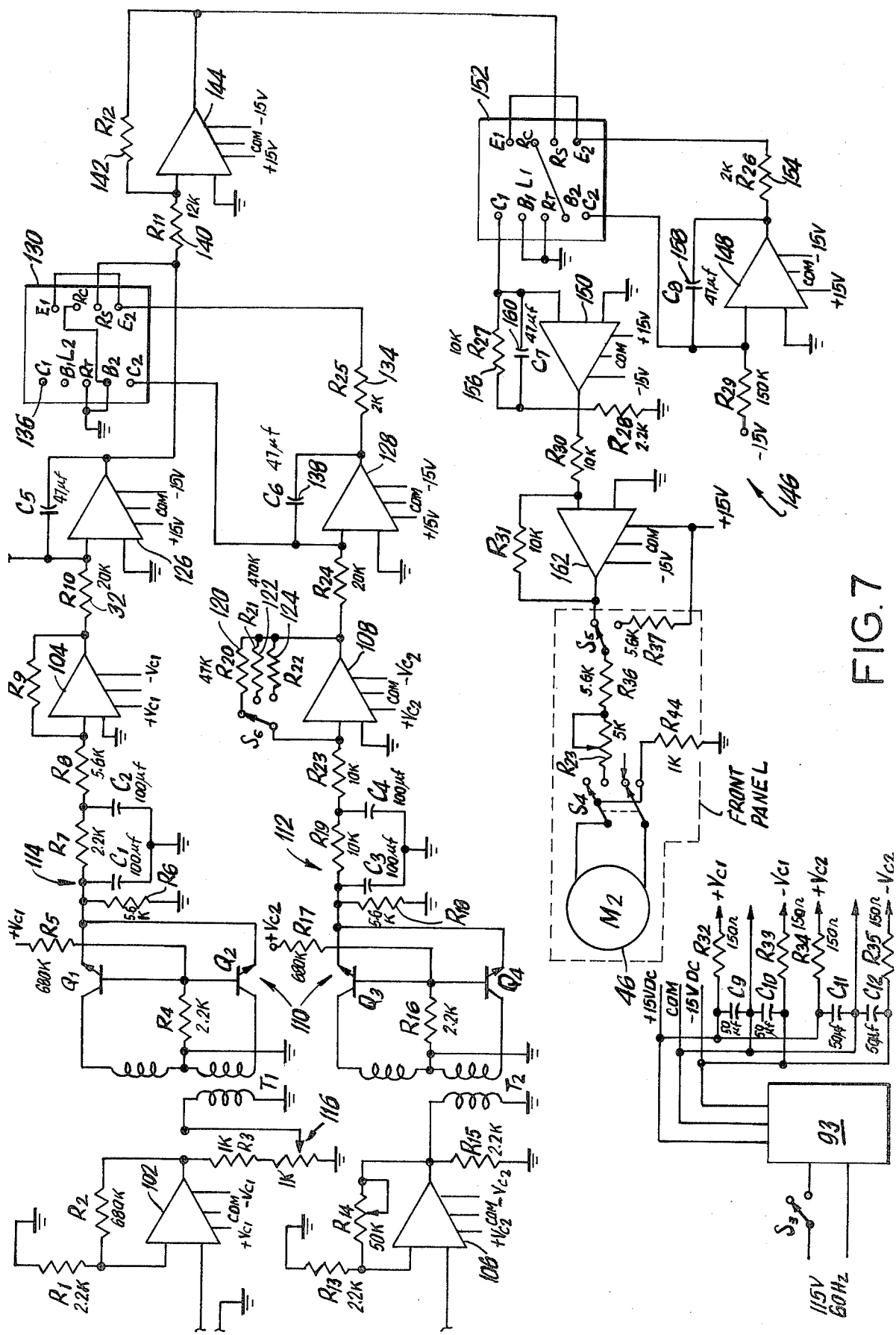
FIG. 7 is a detailed schematic diagram of the dynamic hardness circuit.

Referring to FIG. 7, the dynamic complex hardness circuit 42 is illustrated schematically. This circuit 42 includes its own power supply 93 and circuitry for amplifying, scaling, and converting the AC displacement and force signals received from amplifiers 90 and 92, respectively, to their corresponding DC levels and provide a ratio of these signals

which represents the magnitude of the dynamic complex hardness $|E|$ of the impression roll 10.

The output force signal from amplifier 92 is further amplified by electrically connected operational amplifiers 102 and 104, and the displacement signal from amplifier 90 is further amplified by electrically connected operational amplifiers 106 and 108. AC to DC conversion is provided by a full wave transistor bridge 110 and respective filter networks 112 and 114 electrically coupled between amplifiers 102 and 104, and 106 and 108, respectively. Scaling is attained by potentiometer 116 coupled to the output of amplifier 102 and by adjustments in the gain of amplifiers 106 and 108.

The full wave transistor bridge 110 provides AC to DC conversion and the variable gain amplifiers 106 and 108, including selectable feedback resistors 120, 122, and 124, and the potentiometer 116, boost the d.c. signal amplitudes of the scaled displacement and force transducer output signals and produce equivalent stress and strain d.c. outputs.

Operational amplifiers 126 and 128 are electrically coupled to the outputs of amplifiers 104 and 108, respectively, and to a log amplifier 130. Such a log amplifier is commercially available from Teledyne/Philbrick as Model 4357.

Operational amplifiers 126 and 128, log amplifier 130, input resistor 132, amplifier 126, and feedback capacitors 136 and 138 provide a logarithmic ratio of the stress and strain signals at resistors 140 and 142.

A unity gain amplifier 144 is coupled to the resistor 140 to provide isolation and inversion of the output signal at resistor 140 to drive an anti-log circuit 146 with the logarithmic ratio output.

The anti-log circuit 146 includes an anti-log amplifier 152 coupled to the output of amplifier 144, operational amplifiers 148 and 150 coupled to the anti-log amplifier 152, a resistor 154 coupling the output of the amplifier 148 to the anti-log circuit 152, a feedback resistor 156 for the amplifier 150, feedback capacitors 158 and 160, and a reference current derived from the −15 VDC terminal of the power supply 93 and supplied to the input of the amplifier 148. This circuit 146 provides the anti-log of the input supplied by amplifier 144 to provide a signal proportional to the magnitude of the dynamic complex hardness $|E|$ at the output terminal of amplifier 150.

An amplifier 162 coupled to the output of amplifier 150 provides amplification and isolation for driving the d.c. meter 46.

Figure 8:
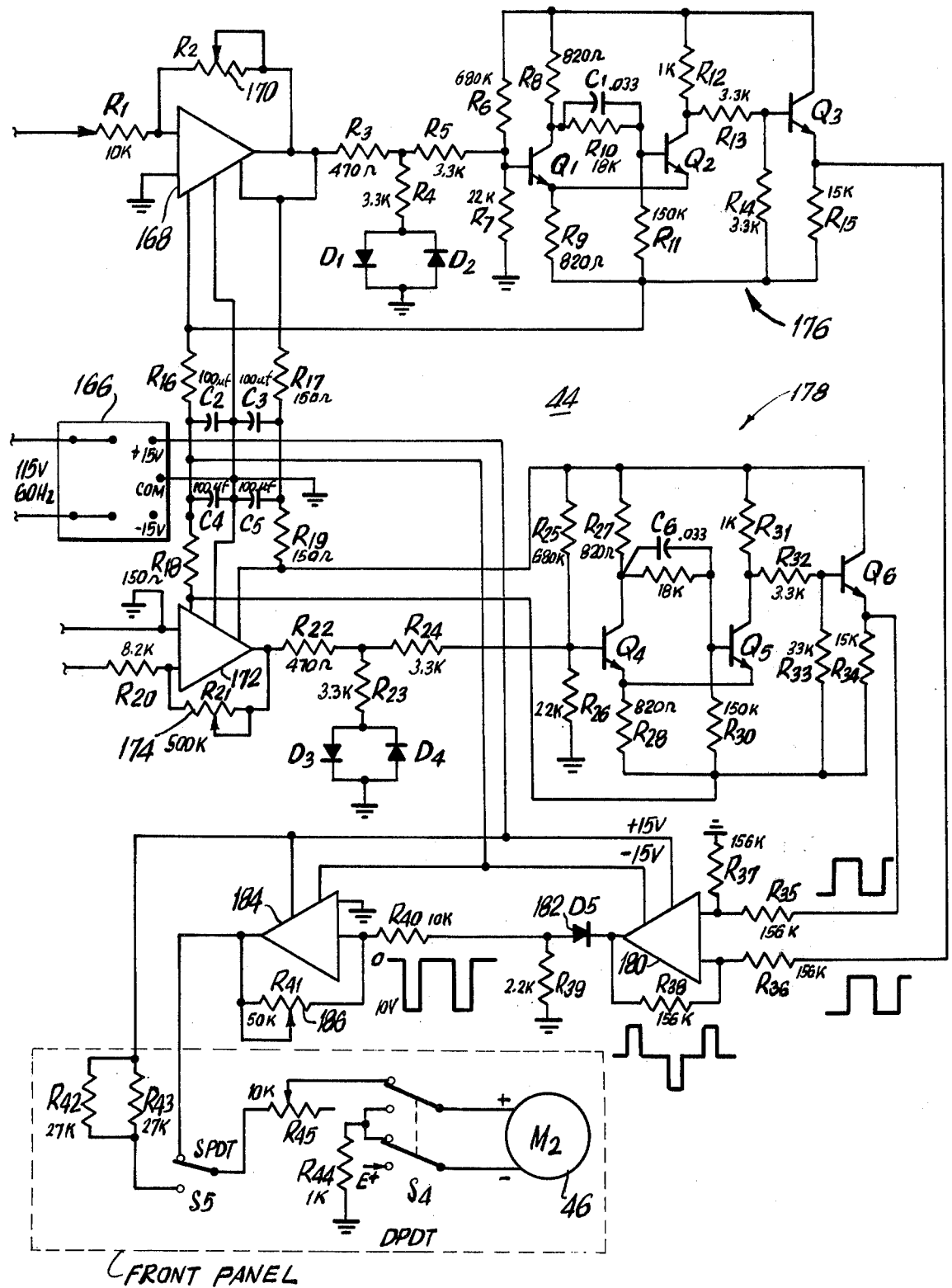
FIG. 8 is a detailed schematic diagram of the loss angle circuit.

Referring to FIG. 8, the phase or loss angle circuit 44 is illustrated. The loss angle is generally indicated by δ and indicates the angle by which the strain or force (F) applied to the impression roll 10 lags the strain or deformation ($d$). The loss angle circuit 44 includes a power supply 166 and the components for amplifying and converting the input sine wave force and displacement signals to square waves and providing a rectangular pulse whose pulse width corresponds to the phase difference between the input force and displacement signals.

Amplification of the input force signal is provided by an operational amplifier 168 having a feedback potentiometer 170. Amplification of the input displacement signal is provided by operational amplifier 172 having a feedback potentiometer 174.

Conversion to square waves is accomplished with multivibrators 176 and 178. The resulting square waves, see FIG. 8, are applied to the input of a differential amplifier 180. The differential amplifier 180 (comparator) produces an output pulse representing the phase difference between the square wave inputs. The positive output pulses are inhibited by diode 182 and the resulting negative pulses are coupled to the output of amplifier 180 and applied to a metering amplifier 184.

The metering amplifier 184, including feedback potentiometer 186, drives the two-scale meter 46 (damped galvanometer) to provide an average readout corresponding to the pulse width. Therefore δ or loss angle is directly determined.

It should be apparent from the foregoing description that the present invention may be modified to provide an indication of the heat generated (heat lost) or power developed in a resilient roll covering in addition to indicating the magnitude and phase angle of the dynamic complex hardness.

It should further be understood by those skilled in the art that various modifications may be made in the present invention without departing from the spirit and scope thereof, as described in the specification and defined in the appended claims.

What is claimed is:

1. Apparatus for determining the dynamic complex hardness of resilient roll coverings, comprising:
   a housing for positioning directly on the resilient roll covering to be tested;
   probe means depending from said housing;
   probe depth control means for adjusting the movement of said probe means for engagement with the resilient roll covering;
   vibrator circuit means for vibrating said probe means to displace the resilient roll covering;
   displacement transducer means coupled to said probe means for providing electrical signals proportional to the displacement (d) of the resilient roll covering;
   force transducer means coupled to said probe means for providing electrical signals proportional to to the force (F) encountered by said probe means during displacement of the resilient roll covering;
   excitation circuit means for energizing said force and displacement transducers and receiving and conditioning output signals from said force and displacement transducers;
   computer circuit means coupled to said excitation circuit means for receiving the force and displacement transducer output signals to provide a direct reading of the magnitude of the dynamic complex hardness

;

and
   phase angle circuit means coupled to said excitation circuit means for receiving the force and displacement transducer output signals to provide a direct reading of the loss angle, δ, therefore, the phase angle between F and d.

2. The apparatus recited in claim 1 wherein:
said housing includes a pair of depending legs having V-shaped notches for positioning directly on a resilient roll covering.

3. The apparatus recited in claim 1 wherein:
said probe means includes a ring with a contact portion extending outwardly therefrom for contact with the resilient roll covering.

4. The apparatus recited in claim 3 wherein:
said force transducer means includes a plurality of strain gauges mounted on said ring of said probe means;
said displacement transducer means includes a core mechanically coupled to said ring of said probe means for movement therewith.

5. The apparatus recited in claim 4 wherein:
said plurality of strain gauges include two pair of strain gauges, said first pair of strain gauges being arranged diametrically opposite each other on the outer surface of said ring, said second pair of strain gauges being arranged diametrically opposite each other on the inner surface of said ring and axially aligned with said first pair.

6. The apparatus recited in claim 5 wherein:
said strain gauges are semiconductor strain gauges.

7. The apparatus recited in claim 1 wherein:
said excitation circuit means includes filtering and attenuating means for applying predetermined input voltages to said force transducer means.

8. The apparatus recited in claim 1 wherein:
said excitation circuit means includes operational amplifiers and potentiometers for conditioning the output signals from said force and displacement transducer means; and
decoupling means for supplying predetermined bias voltages to said operational amplifiers.

9. The apparatus recited in claim 1 wherein:
said computer circuit means includes first circuit means for providing the logarithmic ratio of the conditioned force and displacement signals received from said excitation circuit means, and second circuit means for providing the anti-logarithm of the logarithmic ratio to provide a direct reading of the magnitude of the dynamic complex hardness

.

10. The apparatus recited in claim 9, wherein:
said computer means includes means for amplifying and scaling the conditioned force and displacement signals received from said excitation circuit means and a.c. to d.c. conversion means for converting the a.c. conditioned force and displacement signals received from said excitation circuit means to d.c. signals.

11. The apparatus recited in claim 1, wherein:
said phase angle circuit means includes multivibrator means for converting the conditioned force and displacement signals received from said excitation circuit means to square waves, and comparator means for comparing the square waves and providing an output pulse whose pulse width corresponds to the phase difference between the square waves.

12. Apparatus for determining the dynamic complex hardness of gravure impression rolls for gravure printing, comprising:
- a housing for positioning directly on the gravure impression roll to be tested;
- an adjustable probe means depending from said housing, said adjustable probe means including a ring having a contact portion extending outwardly therefrom;
- vibrator circuit means for vibrating said probe ring to indent the gravure impression roll;
- displacement transducer means coupled to said probe ring for providing electrical signals proportional to the displacement ($d$) of said probe ring and therefore proportional to the displacement of the gravure impression roll;
- force transducer means coupled to said probe ring for providing electrical signals proportional to the force ($F$) encountered by said probe ring during displacement of the gravure impression roll, said force transducer means including a plurality of strain gauges mounted on said probe ring;
- excitation circuit means for energizing said force and displacement transducers and for receiving and conditioning the output signals from said force and displacement transducers;
- computer circuit means coupled to said excitation circuit means for receiving the conditioned output signals from said force and displacement transducers to provide a direct reading of the magnitude of the dynamic hardness

said computer circuit means including the first circuit means for providing the logarithmic ratio of the conditioned force and displacement output signals received from said excitation circuit means, and second circuit means for providing the anti-logarithm of the logarithmic ratio to provide a signal proportional to magnitude of the dynamic complex hardness

and phase angle circuit means coupled to said excitation circuit means for receiving the conditioned output force signals from said force and displacement transducers to provide a direct reading of the loss angle δ, said phase angle circuit means including multivibrator means for converting the conditioned force and displacement signals to square waves, and comparator means for comparing the square waves and providing an output pulse whose pulse width corresponds to the phase difference therebetween.

* * * * *